United States Patent [19]

Kato et al.

[11] Patent Number: 5,772,965

[45] Date of Patent: Jun. 30, 1998

[54] METHOD AND SYSTEM FOR DETECTING DETERIORATION OF EXHAUST GAS CONTROL CATALYST

[75] Inventors: Nobuhide Kato, Aichi-ken; Noriyuki Ina, Okazaki, both of Japan

[73] Assignee: NGK Insulators, Ltd., Japan

[21] Appl. No.: 632,148

[22] Filed: Apr. 15, 1996

[30] Foreign Application Priority Data

Apr. 19, 1995 [JP] Japan .................................. 7-093612

[51] Int. Cl.⁶ .................................................. G01N 27/41
[52] U.S. Cl. ................................ 422/98; 422/83; 422/94; 436/37; 436/137; 436/151; 204/406; 204/427; 73/23.31
[58] Field of Search ........................... 422/83, 90, 92, 422/94, 98; 436/37, 137, 149, 151, 152, 155, 159, 160, 127; 73/23.31, 23.32; 204/406, 427

[56] References Cited

U.S. PATENT DOCUMENTS

| | | |
|---|---|---|
| 4,647,364 | 3/1987 | Mase et al. . |
| 4,755,274 | 7/1988 | Mase et al. . |
| 4,776,943 | 10/1988 | Kitahara .................................. 204/427 |
| 5,250,169 | 10/1993 | Logothetis et al. ...................... 204/424 |
| 5,281,313 | 1/1994 | Visser et al. .......................... 204/153.1 |
| 5,288,375 | 2/1994 | Logothetis et al. ................. 204/153.18 |
| 5,302,275 | 4/1994 | Dietz et al. ............................. 204/424 |
| 5,338,431 | 8/1994 | Yorita et al. ............................. 204/424 |

FOREIGN PATENT DOCUMENTS

| | | |
|---|---|---|
| 2 304 464 | 8/1974 | Germany . |
| 44 08 504 A1 | 9/1995 | Germany . |
| 62-61919 | 4/1987 | Japan . |
| WO 94/15206 | 7/1994 | WIPO . |

OTHER PUBLICATIONS

Patent Abstracts of Japan –vol. 017, No. 250 (P–1537), May 18, 1993 and JP 04 369471 A (Honda Motor Co Ltd), Dec. 22, 1992.

*Primary Examiner*—Jan Ludlow
*Attorney, Agent, or Firm*—Parkhurst & Wendel

[57] ABSTRACT

A system for detecting deterioration of an exhaust gas control catalyst provided in an exhaust gas passage through which a combustion exhaust gas is discharged, including a processing zone communicating with a portion of the passage which is downstream of the catalyst and a pumping cell including an oxygen ion conductive solid electrolyte layer and a pair of electrodes one of which is exposed to the processing zone, wherein the pumping cell pumps oxygen out of the processing zone so as to control oxygen partial pressure in the processing zone which corresponds to a monitor voltage, at a value at which the combustible gas component within the processing zone cannot be burned, and the oxygen concentration in the combustion exhaust gas is obtained based on a pumping current flowing between the pair of electrodes of the pumping cell, whereby the degree of deterioration of the catalyst is determined on the basis of the obtained oxygen concentration.

12 Claims, 5 Drawing Sheets

METHOD AND SYSTEM FOR DETECTING DETERIORATION OF EXHAUST GAS CONTROL CATALYST

BACKGROUND OF THE INVENTION

1. Field of the Invention

The present invention relates in general to a method and a system for detecting deterioration of an exhaust gas control or purification catalyst. In particular, the invention is concerned with such method and system for detecting the deterioration of a catalyst which is adapted to purify a combustion exhaust gas emitted by internal combustion engines of automobiles, and which catalyst is provided in an exhaust emission passage through which the combustion exhaust gas including combustible gas components is discharged. The present invention further relates to a method and an apparatus for measuring the concentration of residual oxygen remaining in the combustion exhaust gas.

2. Discussion of the Prior Art

In an exhaust gas passage through which a combustion exhaust gas emitted by internal combustion engines is discharged, there is conventionally provided a catalyst such as a three way catalyst or an oxidizing catalyst, which is adapted to oxidize and remove combustible gas components included in the combustion exhaust gas. However, such a catalyst tends to deteriorate during a long period of use depending upon its operating condition. Further, catalytic poison components present in the combustion exhaust gas undesirably deteriorate the catalyst. The deterioration of the catalyst results in reduction in its efficiency for purifying the exhaust combustion gas, i.e., catalytic conversion efficiency.

In view of the above, laid-open Publication No. 62-61919 of unexamined Japanese Utility Model application proposes one example of such an apparatus for detecting the deterioration of the exhaust gas control catalyst which is provided in the exhaust gas passage through which the combustion exhaust gas emitted by the internal combustion engine flows. The apparatus disclosed in the publication includes: means for detecting the temperatures of the exhaust gas at an inlet and an outlet of the catalyst, respectively; means for detecting the operating condition of the engine; and means for determining that the catalyst is deteriorated when a difference between the inlet and outlet temperatures of the exhaust gas respectively detected before and after its passage through the catalyst is smaller than a predetermined value, which is determined depending upon the operating condition of the engine.

In an actual operation of the above-described apparatus for detecting the deterioration of the catalyst on the basis of the difference of the inlet and outlet temperatures of the exhaust gas, it is required to control the apparatus to be operative for effecting the determination of deterioration of the catalyst after several minutes of steady running of the vehicle at a constant speed of 40–60 km/hour. This is because a predetermined time is required to thermally stabilize the exhaust system of the vehicle in view of a relatively large heat capacity of the catalyst. For accurate detection of deterioration of the catalyst, a further longer time is required before effecting the determination of deterioration of the catalyst.

In an actual running condition of the vehicle wherein acceleration and deceleration of the vehicle are repeated, it is rather difficult to satisfy the above requirement, i.e., to establish the steady running of the vehicle, under which the apparatus is made operative for effecting the determination. Thus, it is considerably difficult to accurately detect the deterioration of the catalyst on the basis of the difference of the temperatures of the exhaust gas detected at the inlet and outlet of the catalyst. Further, the apparatus as described above inevitably requires two sensors provided at the inlet and outlet of the catalyst for respectively detecting the temperatures of the exhaust gas before and after its passage through the catalyst.

There is widely known an oxygen sensing apparatus for measuring the concentration of oxygen in a combustion exhaust gas which includes: an electrochemical oxygen pumping cell; an oxygen concentration cell; and diffusion control means. In operation, a subject gas in the form of the combustion exhaust gas is introduced into a measuring space in the apparatus under a predetermined diffusion resistance determined by the diffusion control means. The pumping cell is adapted to pump out oxygen from the measuring space and pump in oxygen into the measuring space, such that an electromotive force detected by the oxygen concentration cell is held at a constant level. The thus constructed sensing apparatus is adapted to measure a pumping current which keeps the concentration of oxygen within the measuring space at a constant value.

In the above type of oxygen sensing apparatus, however, combustible gas components such as hydrogen, carbon monoxide or hydrocarbon if included in the subject gas (e.g. combustion exhaust gas) may react with oxygen in the measuring space so as to reduce an amount of oxygen included in the combustion exhaust gas, deteriorating the accuracy of measurement of the oxygen concentration in the exhaust gas.

SUMMARY OF THE INVENTION

The present invention was developed to solve the drawbacks of the known method and apparatus for measuring the oxygen concentration in the combustion exhaust gas. It is therefore a first object of the present invention to provide a method and a system for detecting, with a single sensor, the deterioration of the catalyst with high accuracy in an actual running state of the vehicle, without an influence of heat capacity of the exhaust system including the catalyst.

It is a second object of the invention to provide a method and an apparatus which assure accurate measurement of the oxygen concentration in the combustion exhaust gas without an influence of the combustible gas components included in the combustion exhaust gas.

The above-described first object may be attained according to a first aspect of the invention which provides a method of detecting deterioration of an exhaust gas control catalyst provided in an exhaust gas passage through which a combustion exhaust gas containing a combustible gas component is discharged, comprising the steps of: introducing the combustion exhaust gas which has passed through the catalyst into a processing zone under a predetermined diffusion resistance; energizing an electrochemical oxygen pumping cell to perform an oxygen pumping action for pumping oxygen out of the processing zone to thereby control an oxygen concentration in the combustion exhaust gas within the processing zone to a predetermined value at which the combustible gas component cannot be substantially burned; detecting a pumping current flowing through the electrochemical oxygen pumping cell during energization of the electrochemical pumping cell; and determining a degree of deterioration of the catalyst according to an oxygen concentration in the combustion exhaust gas which is obtained on the basis of the detected pumping current.

The above-indicated first object of the invention may also be attained according to a second aspect of the invention which provides a system for detecting deterioration of an exhaust gas control catalyst provided in an exhaust gas passage through which a combustion exhaust gas containing a combustible gas component is discharged, comprising: a processing zone communicating with a portion of the exhaust gas passage which is downstream of the catalyst as viewed in a direction of flow of the exhaust gas; diffusion control means for introducing, under a predetermined diffusion resistance, the combustion exhaust gas which has passed through the catalyst into the processing zone; an electrochemical oxygen pumping cell including an oxygen ion conductive solid electrolyte layer which partially defines the processing zone, and a pair of electrodes which are disposed in contact with the oxygen ion conductive solid electrolyte layer and one of which is exposed to the processing zone, the electrochemical oxygen pumping cell being energized to perform an oxygen pumping action for pumping oxygen out of the processing zone to thereby control an oxygen concentration in an atmosphere within the processing zone to a predetermined value at which the combustible gas component cannot be substantially burned; detecting means for detecting a pumping current flowing through the electrochemical oxygen pumping cell, during energization of the electrochemical oxygen pumping cell; and means for determining a degree of deterioration of the catalyst according to an oxygen concentration in the combustion exhaust gas which is obtained on the basis of the pumping current obtained by the detecting means.

According to one preferred form of the second aspect of the invention, one of electrodes which is exposed to the processing zone is formed of an electrode material which has substantially no or a small degree of function as an oxidizing catalyst.

The above-indicated second object of the invention may be attained according to a third aspect of the invention which provides a method of measuring a concentration of oxygen in a combustion exhaust gas containing a combustible gas component, comprising the steps of: introducing the combustion exhaust gas into a processing zone under a predetermined diffusion resistance; energizing an electrochemical oxygen pumping cell to perform an oxygen pumping action for pumping oxygen out of the processing zone to thereby control an oxygen concentration in the combustion exhaust gas within the processing zone to a predetermined value at which the combustible gas component cannot be substantially burned; detecting a pumping current flowing through the electrochemical oxygen pumping cell during energization of the electrochemical pumping cell; and obtaining an oxygen concentration in the combustion exhaust gas on the basis of the detected pumping current.

The above-indicated second object of the invention may also be attained according to a fourth aspect of the invention which provides an apparatus for measuring a concentration of oxygen in a combustion exhaust gas containing a combustible gas component, comprising: a processing zone communicating with an exhaust gas passage through which the combustion exhaust gas is discharged; diffusion control means for introducing the combustion exhaust gas from the exhaust gas passage into the processing zone under a predetermined diffusion resistance; an electrochemical oxygen pumping cell including an oxygen ion conductive solid electrolyte layer which partially defines the processing zone, and a pair of electrodes which are disposed in contact with the oxygen ion conductive solid electrolyte layer and one of which is exposed to the processing zone, the electrochemical oxygen pumping cell being energized to perform an oxygen pumping action for pumping oxygen out of the processing zone to thereby control an oxygen concentration in an atmosphere within the processing zone to a predetermined value at which the combustible gas component cannot be substantially burned; and detecting means for detecting a pumping current flowing through the electrochemical oxygen pumping cell, during energization of the electrochemical oxygen pumping cell.

According to one preferred form of the fourth aspect of the invention, one of electrodes which is exposed to the processing zone is formed of an electrode material which has substantially no or a small degree of function as an oxidizing catalyst.

In the present invention, the electrochemical oxygen pumping cell which includes the oxygen ion conductive solid electrolyte layer and a pair of electrodes disposed in contact with the electrolyte layer is energized to perform the oxygen pumping action at a suitable temperature, so that the oxygen partial pressure in the atmosphere which is in contact with one of the pair of electrodes (i.e., cathode) is controlled to a predetermined level which is low enough to inhibit a reaction of oxygen with the combustible gas components existing in the subject gas. Accordingly, the amount of oxygen in the subject gas can be accurately obtained by measuring the electric current flowing between the pair of electrodes.

Described more specifically, the electrochemical oxygen pumping cell performs the pumping action for establishing a condition wherein the reaction of oxygen with the combustible gas components existing in the combustion exhaust gas as the subject gas is inhibited. The pumping current flowing between the pair of electrodes is detected to obtain the concentration of residual oxygen remaining in the combustion exhaust gas, when the oxygen concentration is controlled as described above. Further, the present invention makes it possible to accurately detect the degree of deterioration of the exhaust gas control or purification catalyst, on the basis of the obtained oxygen concentration.

BRIEF DESCRIPTION OF THE DRAWINGS

The above and optional objects, features and advantages of the present invention will be better understood by reading the following detailed description of presently preferred embodiments of the invention, when considered in connection with the accompanying drawings, in which.

DETAILED DESCRIPTION OF THE PREFERRED EMBODIMENTS

There will be first explained a principle of measurement of the oxygen concentration according to the present invention as compared with a conventional oxygen sensor.

Figure 1:
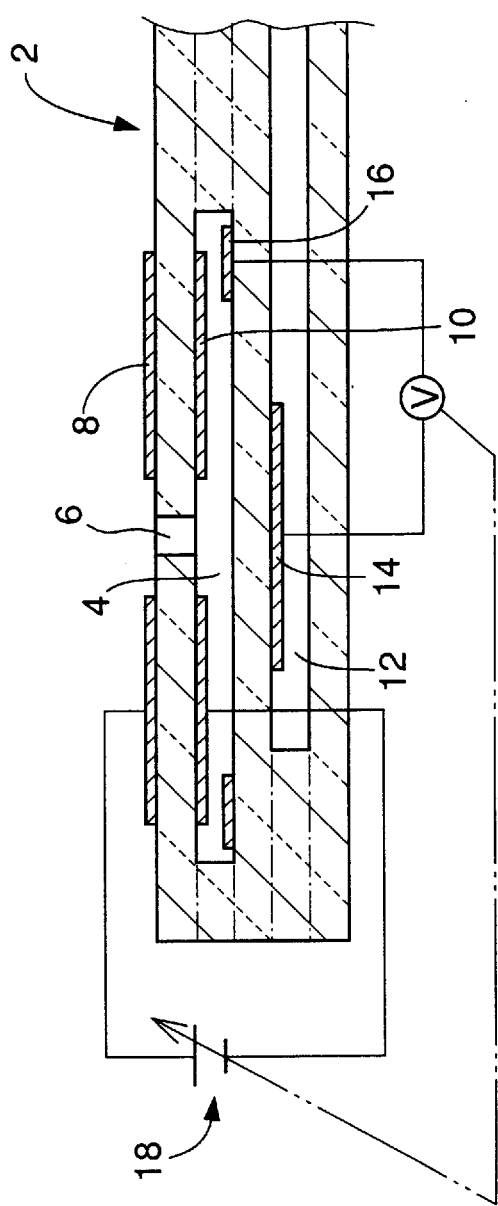
FIG. 1 is an elevational view in longitudinal cross section of one example of a known oxygen sensing element.

Referring to FIG. 1, there is shown a sensing element 2 of the conventional oxygen sensor having an integral laminar structure including a plurality of oxygen ion conductive solid electrolyte layers. Within this sensing element 2, there is formed an internal space 4 as a measuring space which is in communication with an external subject gas space through an orifice 6, which functions as a diffusion control passage having a predetermined diffusion resistance. On the opposite major surfaces of the solid electrolyte layer through which the orifice 6 is formed, there are provided an outer pumping electrode 8 and an inner pumping electrode 10, respectively, so that the above-indicated solid electrolyte layer and the electrodes 8, 10 constitute an electrochemical oxygen pumping cell. The sensing element 2 also has a reference air passage 12 as shown in FIG. 1. On the opposite surfaces of the solid electrolyte layer which partially defines the internal space 4 and the reference air passage 12, there are provided a reference electrode 14 and a measuring electrode 16, so that the above-indicated solid electrolyte layer and the electrodes 14, 16 constitute an electrochemical oxygen sensing cell.

In operation of the oxygen sensing element 2 having the electrochemical oxygen pumping cell and electrochemical oxygen sensing cell constructed as described above, the subject gas is introduced from the external subject gas space into the internal space 4 through the orifice 6 under the predetermined diffusion resistance. The oxygen pumping cell is energized to perform an oxygen pumping action for pumping oxygen out of the internal space 4, at a voltage supplied from a variable-voltage power source 18, which voltage is controlled such that a voltage (monitor voltage) of the oxygen sensing cell is held at a constant level. The operation of the sensing element 2 of the conventional oxygen sensor provides a relationship characteristic of a pumping current (mA) and a monitor voltage (V), as represented by the graph of FIG. 2, as well known in the art.

Figure 2:
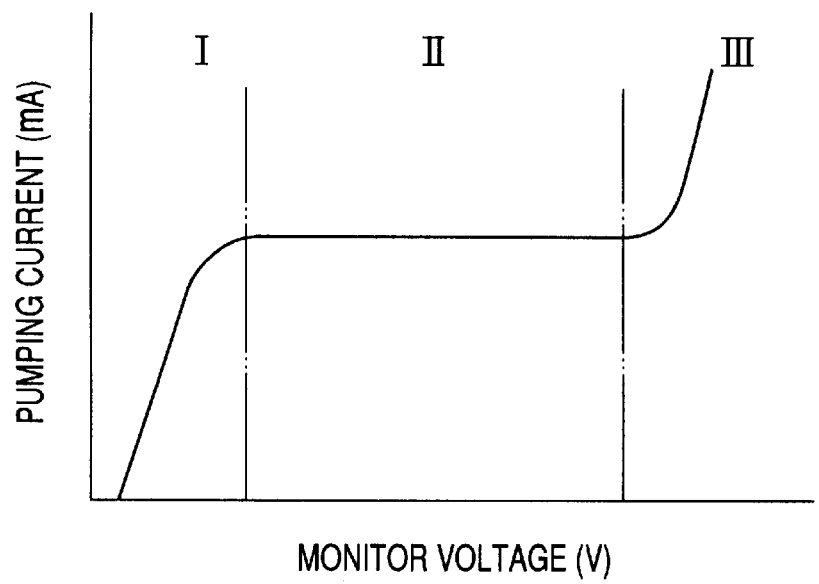
FIG. 2 is a graph indicating a relationship between a pumping current and monitor voltage in the known oxygen sensing element.

In a range indicated by "I" in the graph of FIG. 2, the pumping current increases proportionally to an increase in the monitor voltage (V) corresponding to an electromotive force which is induced between the reference and measuring electrodes 14 and 16 according to a difference in t he oxygen concentration between the atmosphere within the internal space 4 and the reference air within the reference air passage 12. In this first range I, the amount of oxygen which is introduced in to the internal space 4 through the orifice 6 as the diffusion control passage is larger than the amount of oxygen which is pumped out from the internal space 4 into the external subject gas space by the oxygen pumping cell.

With an increase in the monitor voltage, there appears a range "II" wherein the pumping current is held at a constant level irrespective of the increase in the monitor voltage, as shown in the graph of FIG. 2. This second range "II" is referred to as a "current limiting range" in which the amount of oxygen which is introduced through the orifice 6 into the internal space 4 is substantially equal to the amount of oxygen which is pumped out into the external space by the oxygen pumping cell. The conventional oxygen sensing apparatus is operated in this second range II so as to detect the pumping current (limiting current) flowing between the two pumping electrodes 8, 10. Thus, the oxygen concentration in the subject gas is obtained on basis of the detected pumping current since the pumping current in this second range II is proportional to the oxygen concentration in the subject gas.

When the monitor voltage is further increased, there appears a range "III" wherein the pumping current again increases proportionally to the increase in the monitor voltage. In this third range III, the amount of oxygen which is pumped out into the external space by the oxygen pumping cell is larger than the amount of oxygen which is introduced into the space 4 through the orifice 6. Oxygen which is generated by decomposition of a part of carbon dioxide or water included in the subject gas is pumped out in this third range III. With a further increase in the monitor voltage, the solid electrolyte body of the sensing element 2 is decomposed, and the oxygen which is generated by decomposition of the solid electrolyte body is pumped out by the pumping cell.

Figure 3:
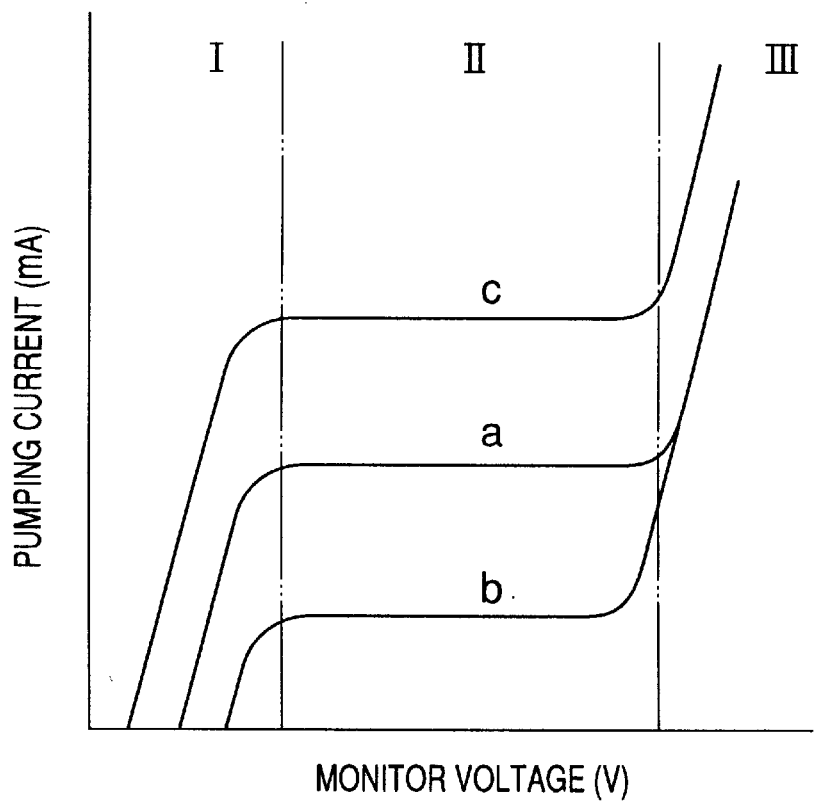
FIG. 3 is a graph indicating a relationship between a pumping current and monitor voltage for explaining a principle of the present invention.

As a result of extensive research by the inventors of the present invention, it was revealed that the pumping current and monitor voltage characteristic (mA-V characteristic) fluctuated as shown in the graph of FIG. 3, depending upon the presence of combustible gas components included in the subject gas and the degree of the oxygen concentration in the subject gas.

In the graph of FIG. 3, a curve indicated by "a" represents a relationship between the monitor voltage and the pumping current, which was obtained when the subject gas included no combustible gas components, while a curve indicated by "b" represents a relationship between the monitor voltage and the pumping current, which was obtained when the subject gas included the combustible gas components. As is apparent from the two curves "a" and "b", the pumping current of the subject gas as represented by the curve "b" is considerably lower than that of the subject gas as represented by the curve "a", in the second range II. This means that, in the second range II, the pumping current is greatly influenced by the presence of the combustible gas components included in the subject gas. On the other hand, in the third range III, the pumping currents as represented by the two curves "a" and "b" are similarly increased with an increase of the monitor voltage. This means that, in the third range III, the pumping current is completely free from the influence of the combustible gas components included in the subject gas. That is, in the third range III, it is possible to obtain the pumping current which accurately reflects the oxygen concentration in the subject gas, regardless of the presence of the combustible gas components in the subject gas.

In the graph of FIG. 3, a curve "c" indicates a relationship between the monitor voltage and the pumping current, which was obtained when the subject gas had a higher oxygen concentration than the subject gas as represented by the curve "a". (The subject gas of the curve "c" included no combustible gas components.) As is apparent from the two curves "a" and "c", the pumping current in the subject gas of the curve "c" is higher than that in the subject gas of the curve "a", in the third range III. This means that, in the third range III, the pumping current varies in proportion to the change in the monitor voltage depending upon the oxygen concentration in the subject gas. Thus, it is possible to obtain the oxygen concentration in the subject gas by detecting the pumping current in the third range III, on the basis of a predetermined relationship between the pumping current and the oxygen concentration.

The present invention was developed based on the findings that the oxidization of the combustible gas components does not occur in the third range III and that the pumping current varies in proportion to the change in the oxygen concentration in the subject gas in the third range III. Described in detail, the present invention provides a technique for accurately measuring the oxygen concentration in the subject gas by detecting the pumping current upon application of a voltage corresponding to a suitably controlled monitor voltage. The technique of the invention is utilized to measure the oxygen concentration in the exhaust combustion gas that contains the combustible gas components and to detect the deterioration of the catalyst for purifying the combustion exhaust gas.

Figure 4A:
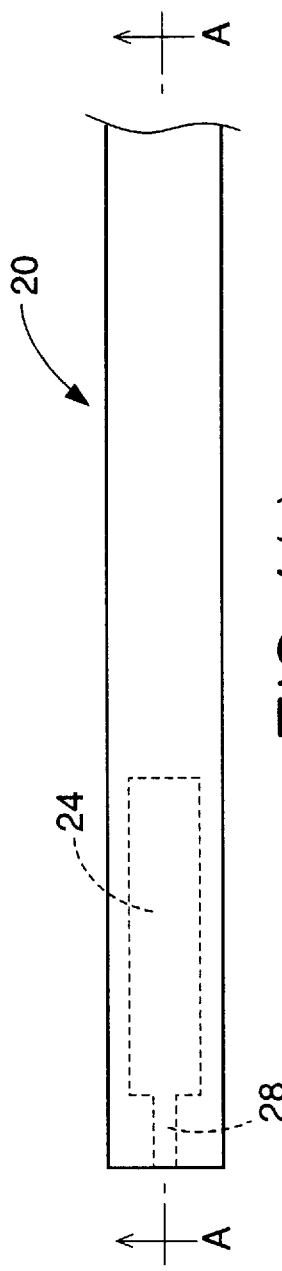
FIG. 4(a) is a fragmentary plan view of an oxygen concentration measuring apparatus constructed according to one embodiment of the present invention.
Figure 4B:
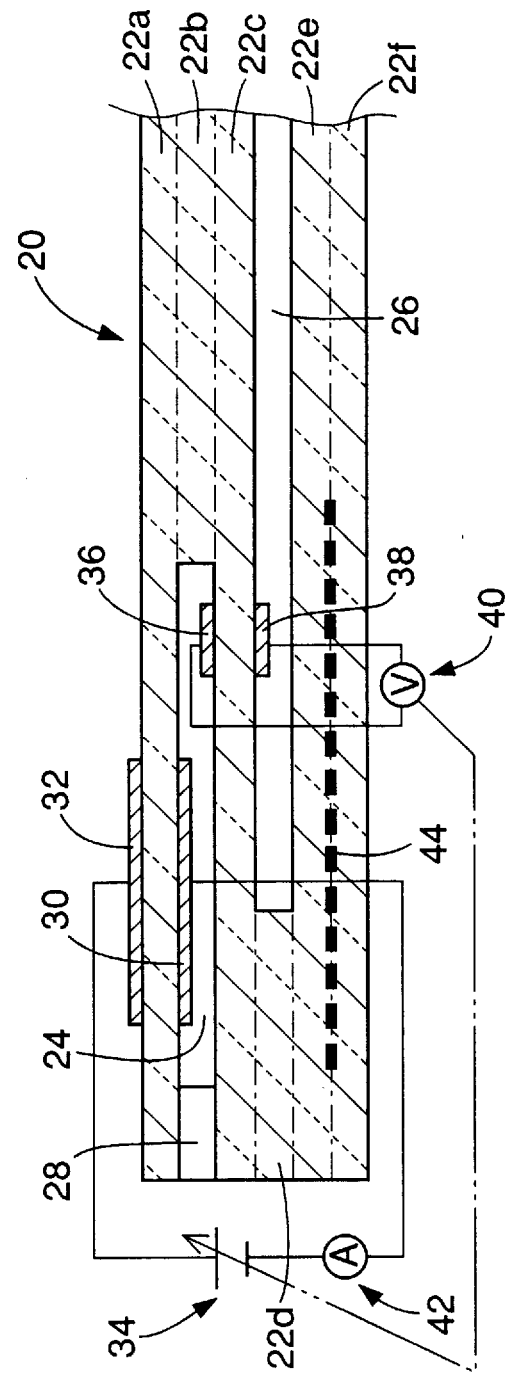
FIG. 4(b) is a fragmentary enlarged view in cross section taken along line A—A of FIG. 4(a)

Referring to FIGS. 4(a) and 4(b), there is shown a typical example of a sensing element 20 used in an apparatus according to one embodiment of the present invention, for measuring the oxygen concentration in a combustion exhaust gas containing combustible gas components.

The sensing element 20 is a plate-like body having a relatively small width and a relatively large length. As is apparent from FIG. 4(b), the plate-like body of the sensing element 20 is an integral laminar structure including a plurality of dense, substantially gas-tight layers 22a, 22b, 22c, 22d, 22e and 22f of oxygen ion conductive solid electrolyte. These solid electrolyte layers 22a–22f are formed of zirconia ceramics or other known oxygen ion conductive solid electrolyte materials. This integral sensing element 20 is produced by co-firing a stack of unfired precursors of the oxygen ion conductive solid electrolyte layers 22a–22f in a manner known in the art.

Within this integral sensing element 20, there is formed an internal cavity 24 which is parallelepipedon as seen in FIGS. 4(a) and 4(b). The internal cavity 24 is formed substantially gas-tightly with respect to the oxygen ion conductive solid electrolyte layers 22a–22f, and provides a processing zone. The sensing element 20 has a reference gas space in the form of a reference air passage 26 which is formed gas-tightly with respect to the internal cavity 24. The reference air passage 26 extends in the longitudinal direction of the sensing element 20, and is open to the ambient atmosphere at one longitudinal end (proximal end) of the sensing element 20.

The internal cavity 24 is defined by a rectangular hole which is formed through the solid electrolyte layer 22b and which is closed by the adjacent upper and lower solid electrolyte layers 22a, 22c. The reference air passage 26 is defined by a rectangular slot which is formed through the solid electrolyte layer 22d and which is closed by the adjacent upper and lower solid electrolyte layers 22c, 22e.

The solid electrolyte layer 22b has a slot which is closed by the adjacent upper and lower solid electrolyte layers 22a, 22c, so as to provide a diffusion control means in the form of a diffusion control passage 28, which is open at the other longitudinal end (distal end) of the sensing element 20. In use, the sensing element 20 is positioned such that the distal end portion at which the diffusion control passage 28 is open is exposed to an external space in which there exists a subject gas (i.e., combustion exhaust gas) including combustible gas components. In operation of the sensing element 20, the combustible exhaust gas is introduced into the internal cavity 24 through the diffusion control passage 28 under a predetermined diffusion resistance. The diffusion control passage 28 functions to limit a rate of flow of the exhaust gas introduced into the internal cavity 24 upon application of a voltage to an electrochemical oxygen pumping cell which will be described, so as to restrict a current flowing through the pumping cell.

A rectangular porous platinum (Pt) inner pumping electrode 30 is provided in contact with an area of the inner surface of the solid electrolyte layer 22a which is exposed to and partially defines the internal cavity 24. Further, a rectangular porous platinum (Pt) outer pumping electrode 32 is provided in contact with an area of the outer surface of the solid electrolyte layer 22a which correspond to the inner surface area on which the inner pumping electrode 30 is provided. These inner and outer pumping electrodes 30, 32 and the solid electrolyte layer 22a constitute an electrochemical oxygen pumping cell. In operation of this oxygen pumping cell, a predetermined voltage is applied from an external variable-voltage power source 34, between the inner and outer pumping electrodes 30, 32, so as to cause a flow of an electric current in a direction from the outer pumping electrode 32 to the inner pumping electrode 30, so that oxygen in the atmosphere in the internal cavity 24 is pumped out into the external subject gas space. In the present sensing element 20, the porous platinum (Pt) pumping electrodes 30, 32 are formed of a cermet consisting of platinum (Pt) as an electrode metal and zirconia ($ZrO_2$) as a ceramic material.

A rectangular porous platinum (Pt) measuring electrode 36 is provided in contact with an area of one of the opposite surfaces of the solid electrolyte layer 22c which is exposed to the internal cavity 24, while a rectangular porous platinum (Pt) reference electrode 38 is provided in contact with the corresponding area of the other surface of the solid electrolyte layer 22c which is exposed to the reference air passage 26. These measuring and reference electrodes 36, 38 and the solid electrolyte layer 22c constitute oxygen partial pressure detecting means in the form of an electrochemical sensing cell. As well known in the art, the sensing cell 22c, 36, 38 is adapted to detect the oxygen partial pressure of the atmosphere in the internal cavity 24 on the basis of an output of a potentiometer 40 indicative of an electromotive force which is induced between the measuring and reference electrodes 36, 38 according to a difference in oxygen concentration between the atmosphere within the internal cavity 24 and the reference air (ambient atmosphere) within the reference air passage 26. The voltage of the variable-voltage power source 34 is controlled based on a voltage (referred to as "monitor voltage" where appropriate) which corresponds to the oxygen partial pressure of the atmosphere in the internal cavity 24 detected by the potentiometer 40, so that the oxygen partial pressure in the internal cavity 24 is held at a predetermined value. The electric current flowing between the inner and outer pumping electrodes 30, 32 upon application of the controlled voltage supplied from the power source 34 is measured by an ammeter 42. This current is referred to as "pumping current".

Within the sensing element 20, there is embedded a heater 44 sandwiched by and between the adjacent upper and lower solid electrolyte layers 22e and 22f. This heater 44 is energized by a suitable external power source. The heater 44 has a resistance (e.g., 9Ω) determined to maintain the temperature in the internal cavity 24 at 600° C., for instance, when the heater 44 is energized with a nominal or rated voltage of 12 V. For electrical insulation of the solid electrolyte layers 22e, 22f from the heater 44, thin electrically insulating layers are formed of alumina or other suitable ceramic material so as to cover the upper and lower surfaces of the heater 44. As shown in FIG. 4(b), the heater 44 has a length sufficient to cover the entire length of the internal cavity 24, so that the space within the internal cavity 24 is uniformly heated to a suitable temperature, to thereby hold the electrochemical oxygen pumping cell (22a, 30, 32) and the electrochemical sensing cell (22c, 36, 38) at substantially the same elevated temperature.

The thus constructed sensing element 20 is positioned such that the distal end portion at which the diffusion control passage 28 is open is exposed to the combustion exhaust gas space, while the proximal end portion at which the reference air passage 26 is open is exposed to the ambient atmosphere. Accordingly, the combustion exhaust gas containing the combustible gas components is introduced into the internal cavity 24 through the diffusion control passage 28 under the predetermined diffusion resistance. The subject gas in the form of the combustion exhaust gas includes combustible gas components such as CO, $H_2$ and HC, as well as gas components such as $N_2$, $O_2$, $CO_2$ and $H_2O$. In operation of the sensing element 20, the electrochemical oxygen pumping cell 22a, 30, 32 is operated to perform an oxygen pumping action by application of the predetermined voltage between the two pumping electrodes 30, 32, whereby oxygen is pumped out from the internal cavity 24 into the external gas space so that the oxygen concentration in the atmosphere in the internal cavity 24 is controlled to a predetermined level which is low enough to inhibit oxidization and burning or combustion of the combustible gas components within the internal cavity 24.

For maintaining the oxygen partial pressure in the internal cavity 24 at the predetermined low level, the electromotive force induced between the measuring and reference electrodes 36, 38 of the electrochemical oxygen sensing cell is measured by the potentiometer 40, and the voltage (supplied from the variable-voltage power source 34) between the two electrodes 30, 32 of the electrochemical oxygen pumping cell is feed-back controlled to control the measured electromotive force to 800 mV at 600° C., for instance. In this case, the oxygen partial pressure of the atmosphere in the internal cavity 24 is controlled to about $10^{-20}$ atm. At this oxygen partial pressure, oxidization and burning or combustion of the combustible gas components such as HC, CO and $H_2$ is substantially impossible. In essence, the voltage to be applied to the electrochemical oxygen pumping cell 22a, 30, 32 is controlled so that the electromotive force which corresponds to a difference between the oxygen concentration in the internal cavity 24 and the oxygen concentration of the reference air corresponds to a desired value of the monitor voltage.

As indicated above, the oxygen partial pressure (oxygen concentration) within the internal cavity 24 is maintained at a level low enough to inhibit the oxidization and burning or combustion of the combustible gas components in the atmosphere within the internal cavity 24, in the presence of the inner and outer pumping electrodes 30, 32, even under heat due to a relatively high temperature of the combustion exhaust gas which exists in the external gas space and due to the elevated temperature (e.g., 600° C.) in the internal space 24 which is heated by the heater 44. Generally, the oxygen partial pressure in the internal cavity 24 is held at $10^{-14}$ atm or lower, preferably, $10^{-16}$ atm or lower. This state of the internal cavity 24 wherein the oxygen partial pressure is held as described above corresponds to the third range III in the graph of FIG. 3. The pumping current flowing between the inner and outer pumping electrodes 30, 32 is detected by the ammeter 42 upon application of the voltage between the two electrodes 30, 32 from the variable-voltage power source 34, such that the voltage corresponds to the monitor voltage that gives the above-indicated state of the internal cavity 24. Since the detected pumping current is proportional to the oxygen concentration in the combustion exhaust gas within the internal cavity 24, and is free from an influence of the combustible gas components, the oxygen concentration in the combustion exhaust gas can be determined or obtained on the basis of the detected pumping current according to a predetermined relationship between the pumping current and the oxygen concentration.

Figure 5:
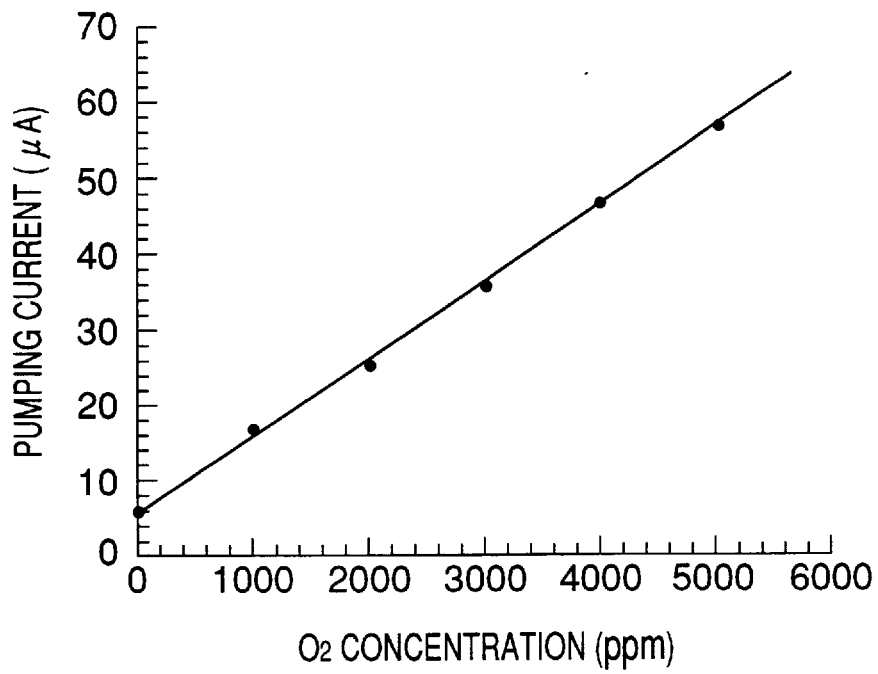
FIG. 5 is a graph indicating a relationship between a pumping current and an oxygen concentration.

The graph of FIG. 5 indicates a change of a pumping current Ip between the inner and outer pumping electrodes 30, 32 of the electrochemical oxygen pumping cell, in relation to the $O_2$ concentration of a standard gas (containing 7% of $H_2O$), when the $O_2$ concentration was changed from 0 to 5000 ppm. The standard gas included nitrogen ($N_2$) as a carrier gas. It will be apparent from the graph of FIG. 5 that the pumping current changes linearly with the change of the $O_2$ concentration. Accordingly, the voltage of the variable-voltage power source 34 is feedback-controlled on the basis of the monitor voltage obtained in the above-described third range III where the $O_2$ concentration is held at a level low enough to inhibit the oxidization and burning or combustion of the combustible gas components. Thus, the $O_2$ concentration in the combustion exhaust gas is obtained based on the detected pumping current flowing through the electrochemical oxygen pumping cell, without the influence of the combustible gas components.

Figure 6:
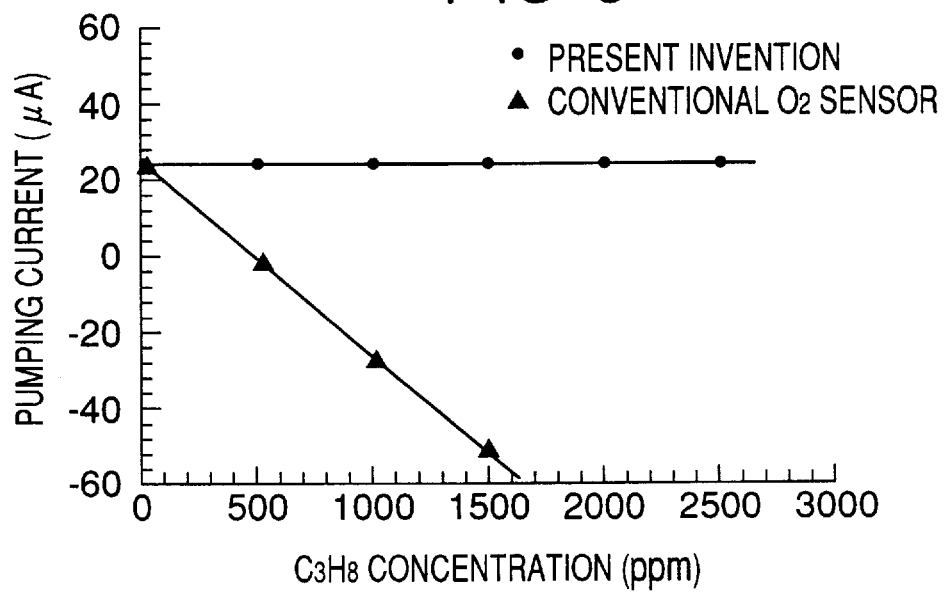
FIG. 6 is a graph indicating a relationship between a pumping current and a $C_3H_8$ concentration.

The graph of FIG. 6 shows interfering characteristics of propane ($C_3H_8$) as the combustible gas component with respect to the pumping current Ip. Described more specifically, the above-described standard gas in which the $O_2$ concentration was 2000 ppm was used. To this standard gas, $C_3H_8$ was added such that the standard gas had different values of $C_3H_8$ concentration. The graph shows the results of measurement of the pumping current which was obtained by the sensing element 20 of the present invention and by the conventional oxygen sensor, respectively. During the pumping action of the electrochemical oxygen pumping cell under the condition where the oxidization of the combustible gas component $C_3H_8$ was inhibited (e.g., 600° C./800 mV), the pumping current was maintained at a constant value in the present sensing element 20 as shown in the graph, without being influenced by the change of the concentration of $C_3H_8$ as the combustible gas component. In contrast, in the conventional oxygen sensor wherein the monitor voltage was controlled to 450 mV (600° C./450 mV) which corresponds to the above-indicated current limiting second range II in the graph of FIG. 3, the pumping current was considerably influenced by the combustible gas component $C_3H_8$ as shown in the graph of FIG. 6, making it impossible to accurately detect the $O_2$ concentration. Thus, it will be apparent that the measurement of the pumping current according to the conventional oxygen sensor does not assure accurate detection of the $O_2$ concentration.

In the present sensing element 20, the oxygen ion conductive solid electrolyte body 22 may be formed of a suitable known material other than zirconia ceramics. Further, the solid electrolyte layers 22a–22f and the various electrodes need not be co-fired. For instance, the electrodes may be formed by baking on the appropriate sintered solid electrolyte layers, and the individual solid electrolyte layers some of which carry the electrodes are then bonded together with a suitable glass material.

The electrodes 30, 32, 36 and 38 are preferably formed of a porous cermet consisting of a mixture of an electrode metal (electrically conductive material) and a ceramic material, for improved adhesion or bonding to the solid electrolyte layers (ceramic substrates). However, these electrodes may consist solely of a metallic material. Of these electrodes, the inner pumping electrode 30 of the electrochemical oxygen pumping cell and the measuring electrode 36 of the electrochemical oxygen sensing cell are preferably formed of a material which has no or only a small degree of function as an oxidizing catalyst. To this end, it is desirable to use Au, Ni or similar electrode material for these electrodes 30, 36. In view of the firing temperature of the solid electrolyte material (e.g., zirconia) in the neighborhood of 1400° C., however, it is desirable to use an alloy of such electrode material (e.g., Au, Ni) and a noble metal having a relatively high melting point such as Pt, Pd and Rh. Although such noble metals have a comparatively high degree of function as the oxidizing catalyst, the function can be made sufficiently small if the alloys include at least 1% of Au, Ni or similar electrode material. For instance, 1% of Au is added to platinum (Pt), and zirconia ($ZrO_2$) is added to this alloy of the electrode materials such that volume ratio of (Pt and Au) to $ZrO_2$ is 60:40. In this instance, the functionality as the oxidizing catalyst of the obtained electrode may be sufficiently reduced.

The electromotive force, i.e., the monitor voltage, detected by the electrochemical oxygen sensing cell is suitably determined depending upon the temperature of the atmosphere within the internal cavity 24 and the selected electrode material, so that the monitor voltage is held within the third range III in the graph of FIG. 3, whereby the $O_2$ concentration of the atmosphere in the internal cavity 24 is controlled to a level low enough to inhibit the burning or combustion of the combustible gas components in the cavity 24. In general, it is preferable to set the monitor voltage at 600–200 mV, more preferably, 700–1500 mV. If the monitor voltage is too low (lower than 600 mV), the combustible gas components in the combustion exhaust gas would be oxidized, making it difficult to accurately obtain the $O_2$ concentration in the cavity 24. On the other hand, if the monitor voltage is too high (higher than 200 mV), there would be a possibility that the obtained $O_2$ concentration is affected by decomposition of $CO_2$ or $H_2O$ present in the combustion exhaust gas. In the third range III, an amount of change of the pumping current with respect to an amount of change of the monitor voltage is relatively large, and the pumping current tends to be influenced by the partial pressures of $H_2O$ and $CO_2$. In view of this, though the monitor voltage is determined to be held within the third range III in the graph of FIG. 3, the monitor voltage is preferably determined to be a value in an area of the third range III which is relatively near the second range II, where the influence of the partial pressures of $H_2O$ and $CO_2$ is comparatively small and the reaction of the combustible gas components with oxygen does not occur.

Figure 7:
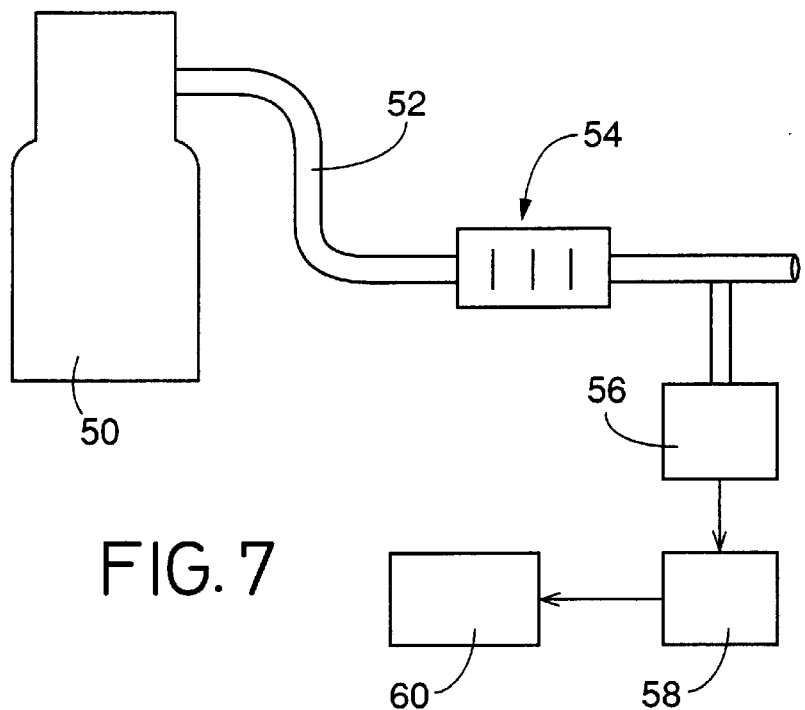
FIG. 7 is a view schematically showing a positional arrangement of one example of a system for detecting the deterioration of an exhaust gas control catalyst, according to the present invention.

Referring next to FIG. 7, there will be explained one example of a system for detecting the deterioration of an exhaust gas control catalyst, which system utilizes the oxygen concentration measuring apparatus constructed as described above.

The combustion exhaust gas containing the combustible gas components is emitted by an internal combustion engine 50 of an automobile, and discharged outside through an exhaust gas passage 52. In the exhaust gas passage 52, there is provided a catalyst 54 in the form of a known oxidizing catalyst or three way catalyst, which is adapted to oxidize and burn the combustible gas components present in the emitted combustion exhaust gas. The catalyst 54 is inspected of its exhaust gas purification efficiency by an oxygen concentration measuring apparatus 56 constructed as shown in FIG. 4, which is disposed at a portion of the exhaust gas passage 52 downstream of the catalyst 54 as viewed in a direction of flow of the combustion exhaust gas from the engine 50. The oxygen concentration measuring apparatus 56 is adapted to inspect the combustion exhaust gas which has passed through the catalyst 54, and determine a degree of deterioration of the catalyst on the basis of the amount of oxygen contained in the combustion exhaust gas. If the catalyst 54 is new enough to exhibit a sufficiently high degree of purification efficiency, the oxygen concentration in the combustion exhaust gas which has passed through the catalyst 54 is lowered by an amount corresponding to an amount of oxygen consumed during oxidization and burning or combustion of the combustible gas components. On the other hand, if the catalyst 54 is deteriorated and has a lowered purification efficiency, the amount of oxygen consumed in oxidization and burning of the combustible gas components within the catalyst 54 is small. Thus, the degree of deterioration of the catalyst 54 is determined by measuring the amount of oxygen contained in the exhaust gas which is fed to the oxygen concentration measuring apparatus 56 through the catalyst 54.

In this arrangement, the combustion exhaust gas passes through the catalyst 54 which is provided in the exhaust gas passage 52, and is introduced into the sensing element 20 of the oxygen concentration measuring apparatus 56 constructed as shown in FIG. 4. In the manner as described above, the sensing element 20 detects the pumping current which corresponds to the oxygen concentration in the combustion exhaust gas which has passed through the catalyst 54. On the basis of the measured pumping current (oxygen concentration), a determining device 58 determines the degree of deterioration of the catalyst 54, and the result of determination is indicated by a display and warning device 60. Namely, the device 60 indicates the degree of deterioration of the catalyst 54 or informs that the catalyst 54 is no more capable of performing a sufficient catalytic action.

In the arrangement of FIG. 7 wherein the oxygen concentration measuring apparatus (56) is positioned at a portion of the exhaust gas passage (52) which is on the downstream side of the exhaust gas control catalyst (54), the pumping current Ip was measured by the oxygen concentration measuring apparatus (56) to inspect the degree of deterioration of the catalyst 54 when the engine (50) was feedback-controlled at the stoichiometric air/fuel ratio.

The engine (50) used in the test was an in-line 4-cylinder engine having a displacement of 2.0 L. As the catalyst (54), there were prepared five specimens A–E. Namely, the specimen A was brand-new, and the other specimens were subjected to aging treatment such that aging times during which the aging treatment was effected on the specimens B, C, D, E increase in the order of description. Each of the thus prepared specimen catalysts A–E was installed in the exhaust gas passage of the engine, and the pumping current Ip was measured to obtain the oxygen concentration in the exhaust combustion gas which has passed through each of the specimens A–E, so as to inspect the degree of deterioration of each specimen. The concentrations of hydrocarbon (HC) in the combustion exhaust gas before and after the passage through the catalyst were respectively obtained according to a known FID method. On the basis of the obtained HC concentrations, HC purification (conversion) efficiency was calculated for each of the specimen catalysts A–E. The results of the measurements are shown in the following TABLE 1.

TABLE 1

| Catalyst | HC Concentration (before passing through catalyst) | HC Concentration (after passing through catalyst) | HC Conversion Efficiency | Pumping Current Ip |
|---|---|---|---|---|
| A | 1640 ppm | 25 ppm | 98.4% | 7 μA |
| B | ↑ | 64 ppm | 96.1% | 10 μA |
| C | ↑ | 168 ppm | 89.8% | 18 μA |
| D | ↑ | 368 ppm | 77.6% | 30 μA |
| E | ↑ | 654 ppm | 60.1% | 51 μA |

It will be apparent from the results of TABLE 1 that the pumping current Ip increases with a decrease in the HC conversion efficiency of the catalyst. Accordingly, the degree of deterioration of the catalyst is determined on the basis of the detected pumping current Ip. For instance, it is determined that the conversion efficiency of the catalyst is lower than a predetermined level when the detected pumping current IP is higher than a predetermined value.

While the presently preferred embodiment of the present invention has been described in detail, for illustrative purpose only, it is to be understood that the invention may be embodied with various changes, modifications and improvements, which may occur to those skilled in the art, without departing from the spirit and scope of the invention.

In the sensing element 20 of FIGS. 4(a) and 4(b), the internal cavity 24 is held in communication with the external gas space through the diffusion control passage 28. However, the internal cavity 24 may directly communicate with the external gas space at the distal end of the sensing element 20. That is, the diffusion control passage 28 may have the same width dimension as the internal cavity 24. For improved stability of the atmosphere in the cavity 24 or for facilitating the control of the atmosphere in the cavity 24, it is desirable that the cross sectional area of the diffusion control passage 28 be smaller than that of the internal cavity 24.

Figure 8:
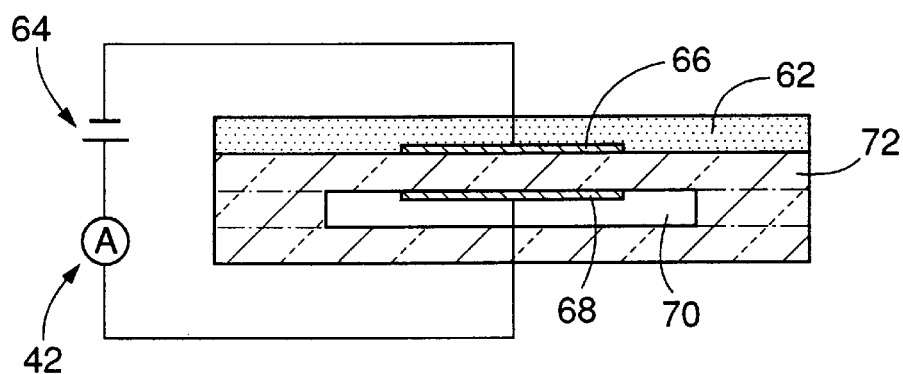
FIG. 8 is a longitudinal cross sectional view showing another embodiment of the oxygen concentration measuring apparatus of the present invention.

The diffusion control passage 28 as the diffusion control means in the illustrated embodiment may be replaced with a porous layer 62 as shown in FIG. 8, through which the combustion exhaust gas is introduced into the sensing element 20 under a predetermined diffusion resistance. In the illustrated embodiment, the monitor voltage measured in the electrochemical oxygen sensing cell is detected to feedback-control the voltage of the variable-voltage power source 34 to be applied between the two pumping electrodes 30, 32 of the electrochemical oxygen pumping cell. However, the detection of the monitor voltage may be eliminated. In this case, a predetermined constant voltage is applied from a constant-voltage power source 64 between pumping electrodes 66, 68 of the electrochemical oxygen pumping cell, so that oxygen in the combustion exhaust gas which is present around the pumping electrode 66 is pumped into an atmosphere communication passage 70. The pumping current between the two electrode 66, 68 is measured by the ammeter 42 to obtain the concentration of the oxygen in the atmosphere communication passage 70. In FIG. 8, the reference numeral 72 indicates a solid electrolyte body.

Figure 9:
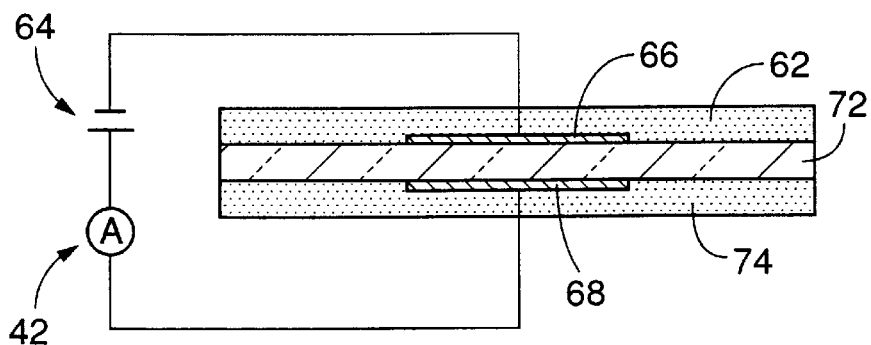
FIG. 9 is a longitudinal cross sectional view showing sill another embodiment of the oxygen concentration measuring apparatus of the present invention.

As shown in FIG. 9, the pumping electrode 68 through which oxygen is pumped out may be covered by a porous body 74, so that oxygen pumped out by the electrochemical pumping cell is retained around the pumping electrode 68 and utilized as reference oxygen. In this case, the electromotive force induced between the two electrodes 66, 68 is superimposed, whereby the voltage supplied from the constant-voltage power source 64 can be lowered.

The sensing element 20 may be constructed with various other modifications which may occur to those skilled in the art. For instance, the configuration of the sensing element 20 is by no means limited to the plate-like body of the illustrated embodiment, but may be a cylindrical body. Further, the reference electrode 38 and the outer pumping electrode 32 which are disposed in the reference air passage 26 may be constructed as a common electrode.

According to the method and system for detecting deterioration of the exhaust gas control catalyst of the present invention, the concentration of oxygen remaining in the combustion exhaust gas can be accurately obtained without being influenced by the combustible gas components contained in the combustion exhaust gas. Further, it is possible to properly determine the degree of deterioration of the catalyst on the basis of the obtained oxygen concentration. The present method is effectively utilized in an apparatus and method for accurately measuring the concentration of oxygen in the combustion exhaust gas which contains the combustible gas components.

What is claimed is:

1. A system for detecting deterioration of an exhaust gas control catalyst provided in an exhaust gas passage through which a combustion exhaust gas containing a combustible gas component is discharged, comprising:

a processing zone in fluid communication with a portion of said exhaust gas passage which is downstream of said catalyst as viewed in a direction of flow of said exhaust gas;

diffusion control means for introducing, under a predetermined diffusion resistance, said combustion exhaust gas which has passed through said catalyst into said processing zone;

an electrochemical oxygen pumping cell including an oxygen ion conductive solid electrolyte layer which partially defines said processing zone, and a pair of electrodes which are disposed in contact with said oxygen ion conductive solid electrolyte layer and one of which is exposed to said processing zone;

means for energizing said electrochemical oxygen pumping cell to perform an oxygen pumping action for pumping oxygen out of said processing zone to thereby control an oxygen concentration in an atmosphere within said processing zone to a predetermined value at which said combustible gas component cannot be substantially burned;

detecting means for detecting a pumping current flowing through said electrochemical oxygen pumping cell, during energization of said electrochemical oxygen pumping cell;

oxygen partial pressure detecting means for detecting an oxygen partial pressure of said atmosphere within said processing zone;

a variable-voltage power source for applying a voltage between said pair of electrodes of said electrochemical oxygen pumping cell;

means for controlling said power source in response to a signal from said oxygen partial pressure detecting means such that said voltage is controlled on the basis of a monitor voltage, said monitor voltage being maintained in a range of 600–2000 mV, which corresponds to said oxygen partial pressure detected by said oxygen partial pressure detecting means, to thereby control said oxygen pressure of said atmosphere within said processing zone; and means for determining a degree of deterioration of said catalyst according to an oxygen concentration in said combustion exhaust gas which is obtained on the basis of said pumping current obtained by said detecting means.

2. A system according to claim 1, wherein said one of said electrodes which is exposed to said processing zone is formed of an electrode material which has substantially no ability to function as an oxidizing catalyst.

3. A system according to claim 1, wherein said processing zone, said diffusion control means and said electrochemical oxygen pumping cell are integrally provided in a sensing element which includes said oxygen ion conductive solid electrolyte layer as an integral part thereof, said sensing element having an internal cavity which provides said processing zone and communicates with said portion of said exhaust gas passage which is downstream of said catalyst as viewed in the direction of flow of said combustion exhaust gas.

4. A system according to claim 3, wherein said diffusion control means is formed in communication with said internal cavity and is open to said portion of said exhaust gas passage which is downstream of said catalyst as viewed in said direction.

5. A system according to claim 1, further comprising heating means for heating said electrochemical oxygen pumping cell to a predetermined temperature.

6. An apparatus according to claim 1, wherein said diffusion control means consists of a porous layer formed on one of said pair of electrodes.

7. An apparatus for measuring a concentration of oxygen in a combustion exhaust gas containing a combustible gas component, comprising:

a processing zone in fluid communication with an exhaust gas passage through which said combustion exhaust gas is discharged;

diffusion control means for introducing said combustion exhaust gas from said exhaust gas passage into said processing zone under a predetermined diffusion resistance;

an electrochemical oxygen pumping cell including an oxygen ion conductive solid electrolyte layer which partially defines said processing zone, and a pair of electrodes which are disposed in contact with said oxygen ion conductive solid electrolyte layer and one of which is exposed to said processing zone;

means for energizing said electrochemical oxygen pumping cell to perform an oxygen pumping action for pumping oxygen out of said processing zone to thereby control an oxygen concentration in an atmosphere within said processing zone to a predetermined value at which said combustible gas component cannot be substantially burned;

oxygen partial pressure detecting means for detecting an oxygen partial pressure of said atmosphere within said processing zone; and a variable-voltage power source for applying a voltage between said pair of electrodes of said electrochemical oxygen pumping cell;

means for controlling said power source in response to a signal from said oxygen partial pressure detecting means such that said voltage is controlled on the basis of a monitor voltage, said monitor voltage being maintained in a range of 600–2000 mV. which corresponds to said oxygen partial pressure detected by said oxygen partial pressure detecting means, to thereby control said oxygen pressure of said atmosphere within said processing zone; and detecting means for detecting a pumping current flowing through said electrochemical oxygen pumping cell, during energization of said electrochemical oxygen pumping cell.

8. An apparatus according to claim 7, wherein said one of said electrodes which is exposed to said processing zone is formed of an electrode material which has substantially no ability to function as an oxidizing catalyst.

9. An apparatus according to claim 7, wherein said processing zone, said diffusion control means and said electrochemical oxygen pumping cell are integrally provided in a sensing element which includes said oxygen ion conductive solid electrolyte layer as an integral part thereof, said sensing element having an internal cavity which provides said processing zone and communicates with said exhaust gas passage.

10. An apparatus according to claim 9, wherein said diffusion control means is formed in communication with said internal cavity and is open to said exhaust gas passage.

11. An apparatus according to claim 7, further comprising heating means for heating said electrochemical oxygen pumping cell to a predetermined temperature.

12. An apparatus according to claim 7, wherein said diffusion control means consists of a porous layer formed on one of said pair of electrodes.

* * * * *